(12) United States Patent
Liepa

(10) Patent No.: US 6,563,010 B1
(45) Date of Patent: May 13, 2003

(54) ADSORBENT BED LOADING AND REGENERATION

(75) Inventor: Mark A. Liepa, Exton, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/161,004

(22) Filed: Jun. 3, 2002

(51) Int. Cl.⁷ .......................... C07C 27/34; C07C 29/76
(52) U.S. Cl. ...................... 568/917; 210/673; 210/670; 210/676
(58) Field of Search .................................. 568/913, 917, 568/868; 210/660, 661, 663, 669, 670, 673, 675, 676, 690, 150, 151

(56) References Cited

U.S. PATENT DOCUMENTS

| 4,239,926 A | 12/1980 | Grane et al. |
| 4,543,432 A | 9/1985 | Shen et al. |
| 6,037,516 A | 3/2000 | Morford et al. |
| 6,069,287 A | 5/2000 | Ladwig et al. |
| 6,133,484 A | 10/2000 | Knifton et al. |

*Primary Examiner*—Johann Richter
*Assistant Examiner*—Elvis O. Price
(74) *Attorney, Agent, or Firm*—William C. Long

(57) ABSTRACT

The process for removing impurities from a liquid by contact with a solid adsorbent using parallel contact adsorbent beds such that when one bed is contacting the liquid the parallel bed is being regenerated by contact with heated inert gas, wherein during changeover of the beds inert gas is transferred from the regenerated bed to the spent bed during the period that liquid is being drained from the spent bed.

4 Claims, 4 Drawing Sheets

FIG. 1 BED 1 LOADING AND BED 2 REGENERATING
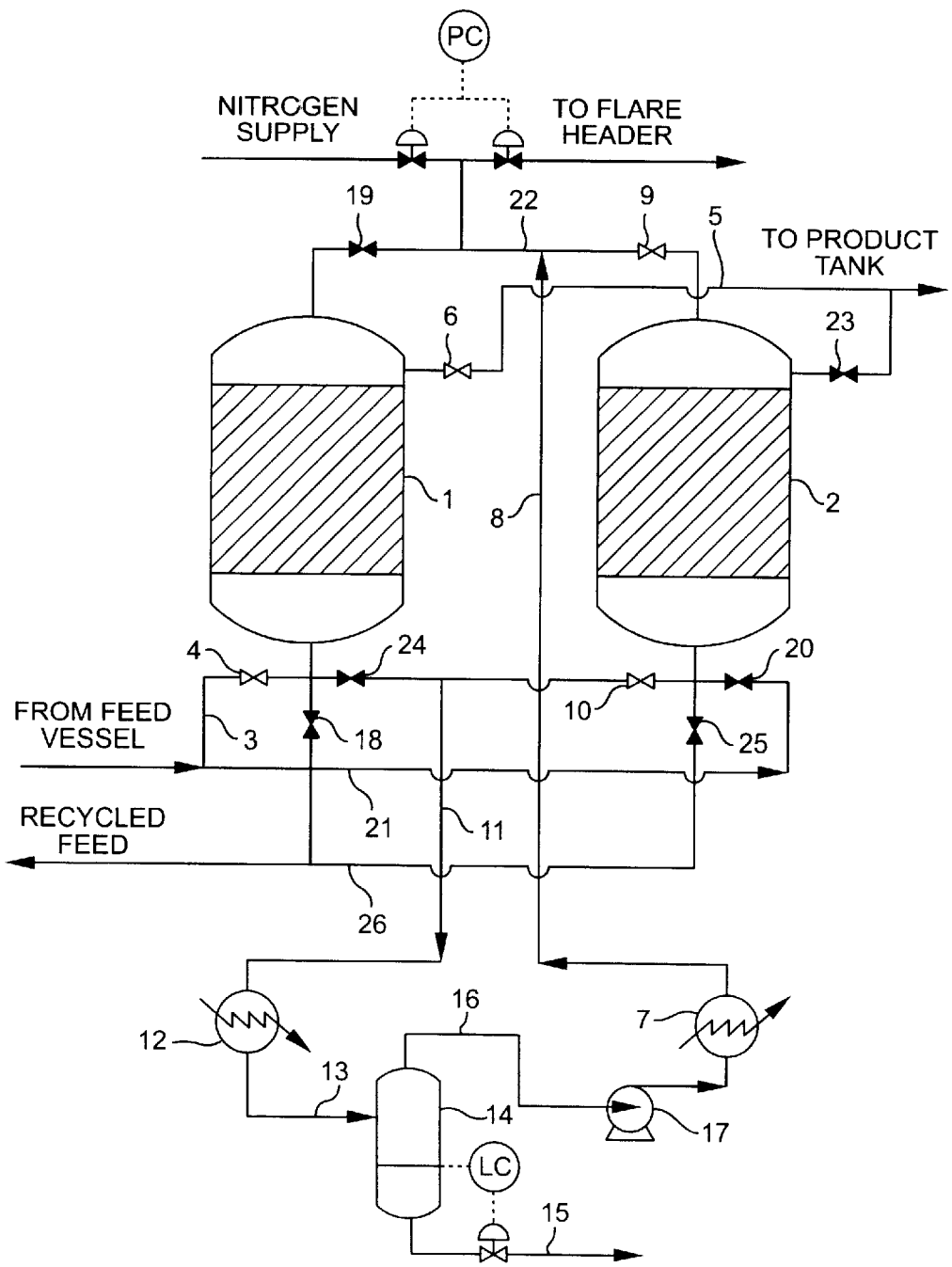

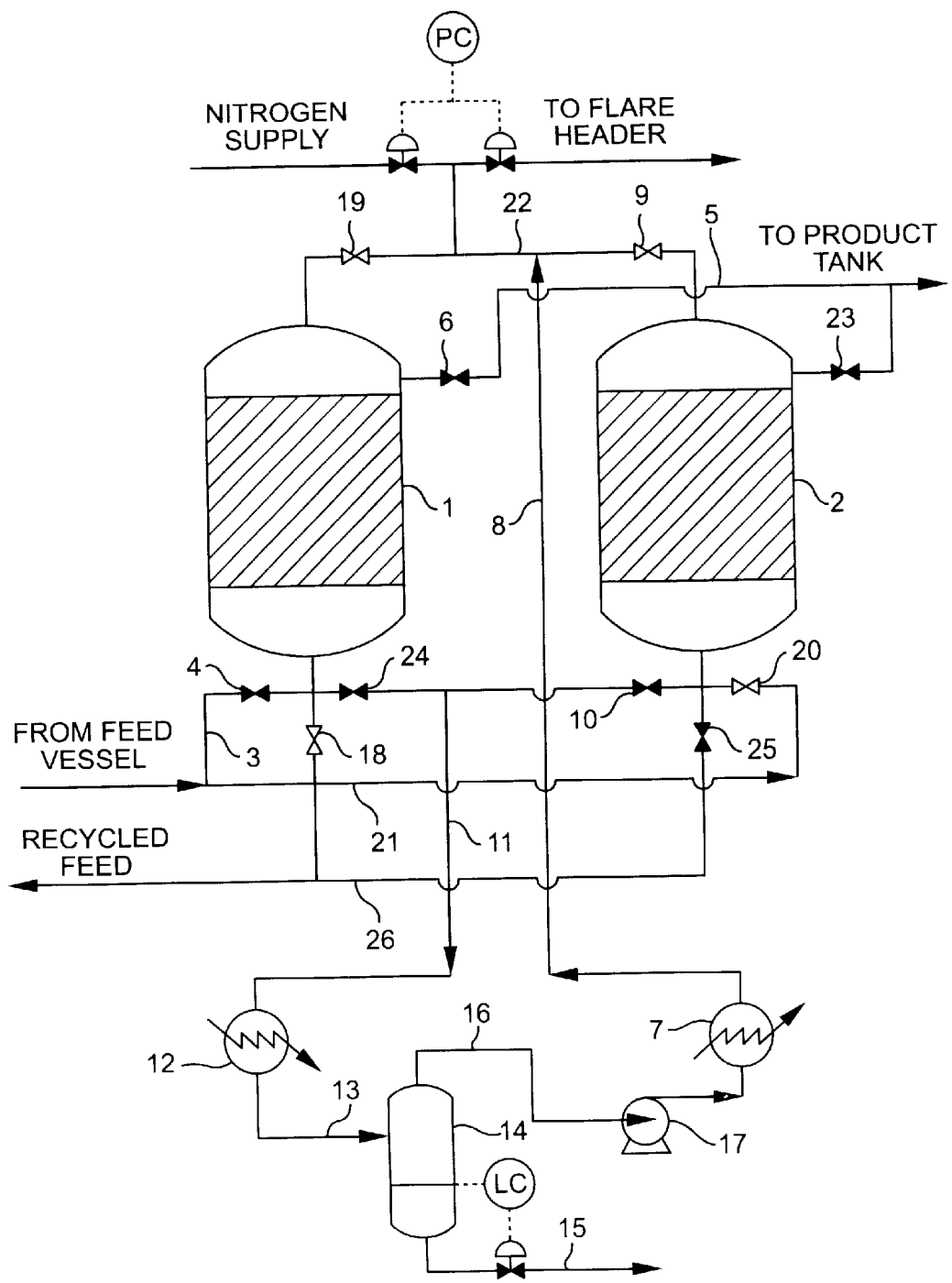
FIG. 2  BED 1 DRAINING AND BED 2 FILLING

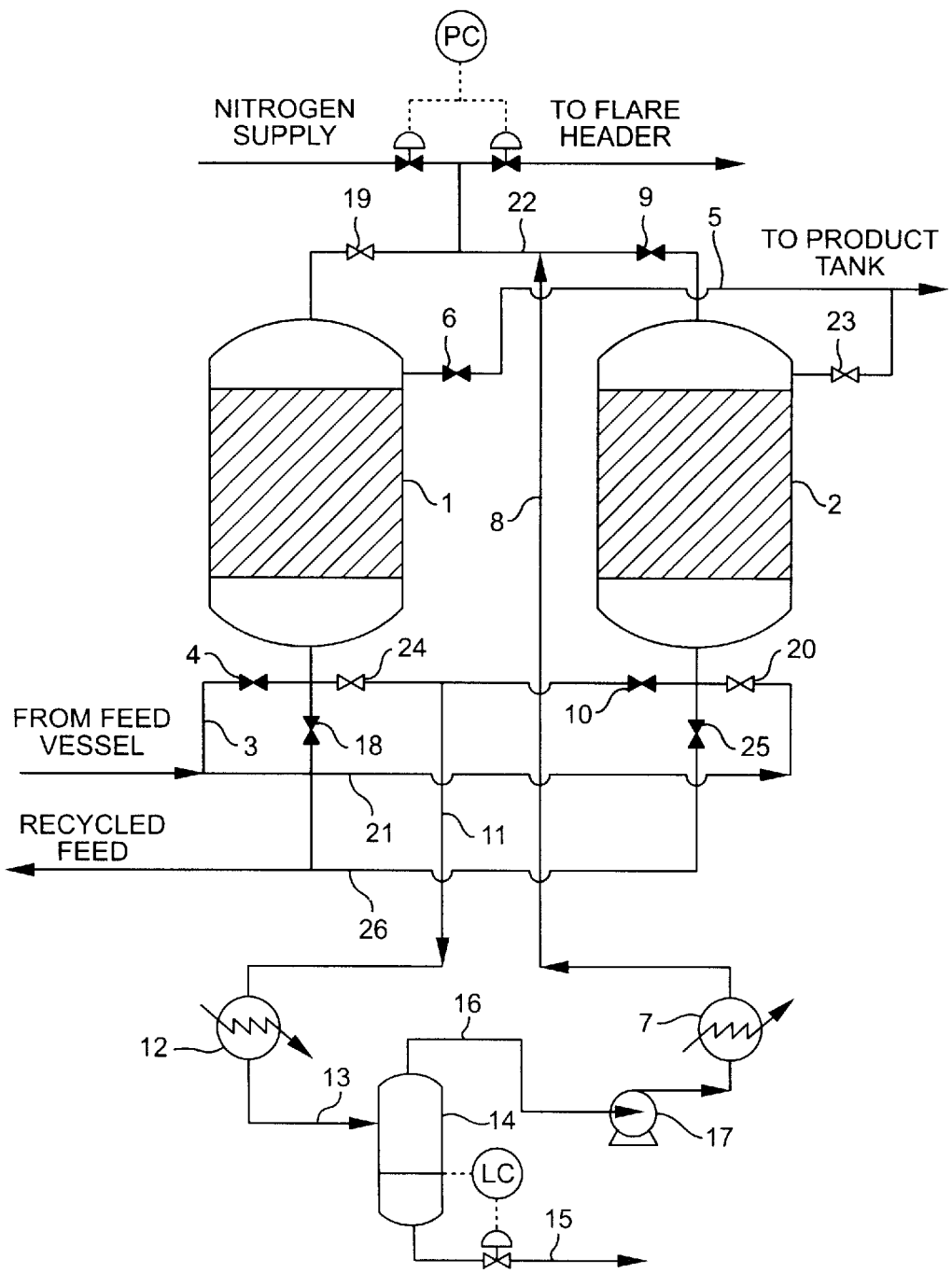
FIG. 3 BED 1 REGENERATING AND BED 2 LOADING

FIG. 4  BED 1 FILLING AND BED 2 DRAINING
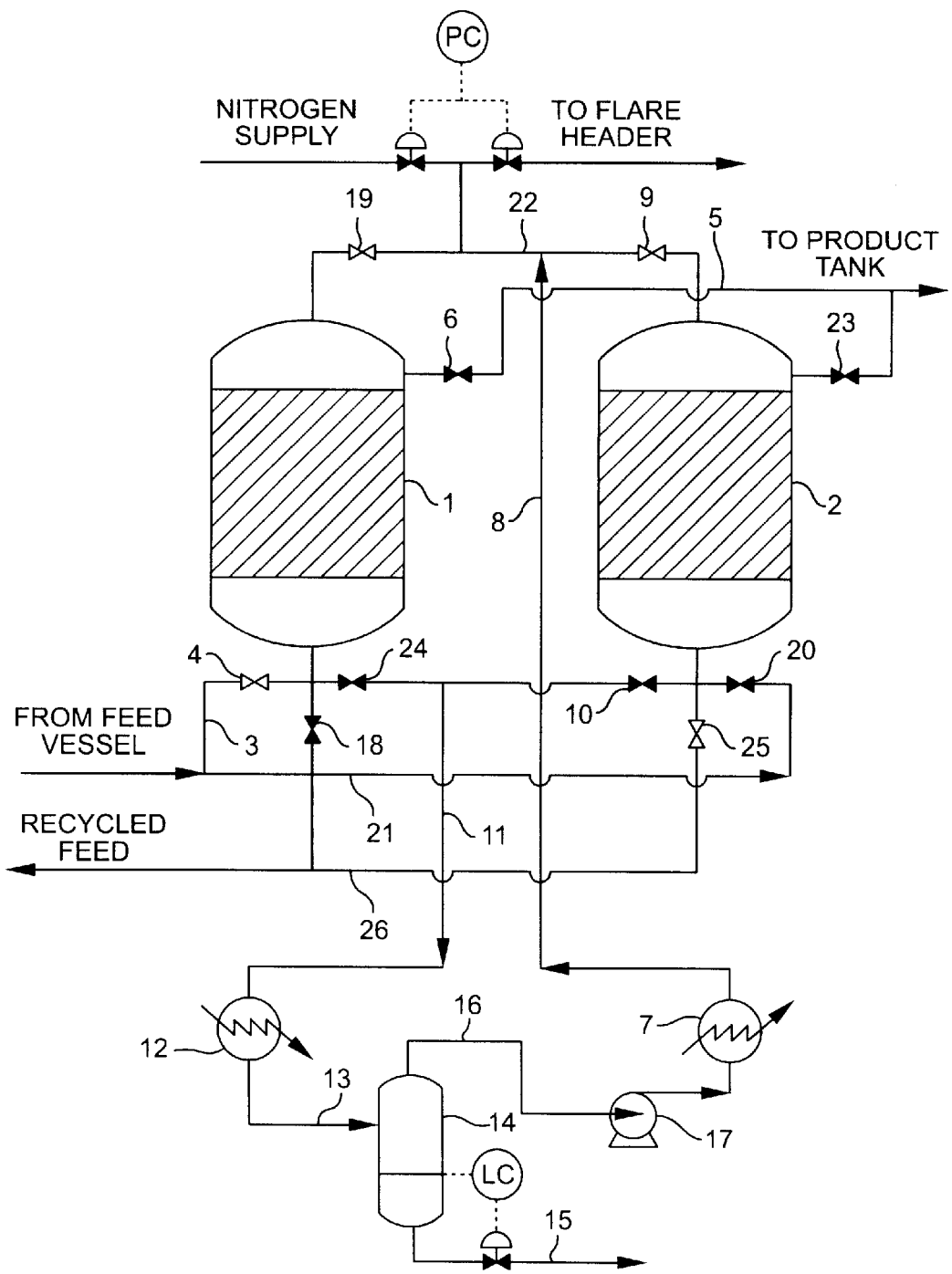

ADSORBENT BED LOADING AND REGENERATION

BACKGROUND OF THE INVENTION

1. Field of the Invention

The present invention relates to an improved system and process for the loading and hot gas regeneration of adsorbent beds which are used in the purification of liquids such as tertiary butyl alcohol and the like.

2. Description of the Prior Art

Liquids such as tertiary butyl alcohol and the like are treated in order to remove impurities by passing the liquid through a bed of suitable solid adsorbent particles. When the maximum contaminant adsorption or loading is reached, the adsorbent bed can be regenerated by draining liquid from the bed and then stripping the contaminants into a stream of hot gas such as nitrogen.

For continuous operation it is advantageous to operate with two adsorbent beds in parallel with one bed being used to adsorb contaminants from the liquid being treated while at the same time the second bed is being regenerated.

A problem arises during the changeover where the bed which has reached its desired capacity to remove contaminants is to be regenerated and the bed which has been regenerated is to be placed in service to remove contaminants from the liquid being treated.

The bed which has reached its capacity and which is to be regenerated is drained of liquid with an inert gas such as nitrogen being provided to replace the drained liquid while the bed of regenerated adsorbent is filled with liquid and inert gas is vented therefrom.

Significant expenses are incurred as a result of venting the inert gases as an increased load is placed on a plant contaminated gas handling system, as well as the cost of replacing the vented inert gas.

The present invention relates to an improved method and system for carrying out parallel bed adsorption and regeneration while substantially avoiding the disadvantages of the prior art.

SUMMARY OF THE INVENTION

In accordance with the invention parallel adsorption beds are provided with connecting means such that under normal operation a liquid to be treated is passed through one bed while separately the second bed is being purged with a heated inert gas, and during the changeover period while the regenerated bed is filling with liquid to be treated, inert gas is displaced and passes to the depleted bed which is being drained preparatory to regeneration.

DESCRIPTION OF THE DRAWINGS

FIG. 1 illustrates operation of the system where the first adsorptive bed is removing contaminants and the second bed is being regenerated.

FIG. 2 illustrates operation during the changeover when the first bed is drained and the second bed filled.

FIG. 3 illustrates operation of the system where the first bed is being regenerated and the second bed is removing contaminants.

FIG. 4 illustrates operation during the changeover when the second bed is drained and the first bed filled.

DETAILED DESCRIPTION

Referring to FIG. 1, beds 1 and 2 are conventional vessels each packed with a bed of solid adsorbent. In operation illustrated in FIG. 1, liquid from which contaminants are to be adsorbed is passed from a feed vessel (not shown) via line 3 through open valve 4 into bed 1. The liquid passes through the adsorptive bed and passes from bed 1 via line 5 through open valve 6 to a product tank (not shown).

While liquid is being treated in bed 1, the bed 2 adsorptive solid is being regenerated. Inert gas is heated in heater 7 and passes via line 8 through open valve 9 and then through bed 2 of adsorptive solid, stripping contaminants from the solid. The inert gas containing stripped contaminants passes from bed 2 through open valve 10 via line 11 to cooler 12 and then via line 13 to liquid/vapor separator 14. Condensed impurities are separated as liquid via line 15 and the inert gas passes via line 16 to blower 17 and thence to heater 7 and back to adsorptive bed 2 via line 8.

After a certain time of operation as described above, the contaminant adsorption capacity in bed 1 decreases to the point at which the bed should be regenerated.

Referring to FIG. 2, valves 4 and 6 are closed, and valves 18 and 19 are opened. Valve 10 is closed and valve 20 is opened whereupon liquid to be treated passes via line 21 through valve 20 to fill bed 2. As the liquid fills bed 2, inert gas is displaced via line 22 through valves 9 and 19 into bed 1. Liquid is drained from bed 1 through open valve 18 and line 26 to be recycled.

By such operation, loss of inert gas as bed 2 is filled and bed 1 drained is essentially avoided.

After bed 1 is drained and bed 2 filled, with liquid, operation is continued as shown in FIG. 3.

Referring to FIG. 3, liquid to be treated passes via line 21 through valve 20 and through bed 2. Treated liquid passes through open valve 23 via line 5 to the product tank. Valve 9 is closed to prevent communication between beds 1 and 2 during this operation.

At the same time heated inert gas passes from heater 7 via line 8 through open valve 19 into bed 1 wherein it strips contaminants from the adsorptive solid.

Vapor containing stripped contaminants passes from bed 1 through open valve 24 and thence to cooler 12 and separator 14 which are operated as above described. Valve 18 is closed during this operation.

When the adsorptive capacity of solids in bed 2 has decreased to the point where regeneration is advisable, operation is changed to that described in FIG. 4.

Referring to FIG. 4, valves 23 and 20 are closed and liquid is drained through open valve 25 and line 26 to be recycled. Valve 9 is opened to permit inert gas to pass from bed 1 to bed 2 as bed 1 is filled. Liquid to be treated passes into bed 1 via line 3 and open valve 4 and displaced inert gas passes from bed 1 through valve 19, line 22 and valve 9 to bed 2.

When bed 1 is filled and bed 2 is drained, operation resumes as described above for FIG. 1.

Practice of the invention is especially applicable to the purification of tertiary butyl alcohol using sodium form large pore zeolites as described, for example, in commonly assigned copending U.S. patent application Ser. No. 10/005,110 filed Dec. 03, 2001 the disclosure of which is incorporated herein by reference. However, the invention is broadly applicable to systems wherein a plurality of adsorptive solid beds are used to treat liquids.

EXAMPLE

Referring to FIGS. 1–4, contact vessels 1 and 2 are each packed with particulate Zeolite 13X, a large pore zeolite in the sodium form.

The liquid feed to the system is tertiary butyl alcohol produced by the Oxirane process and comprising by weight about 97% TBA, 0.13% methanol, 0.51% water, 0.66% acetone, 0.26% IPA, 0.11% MEK, 0.04% SBA, 0.39%TBF, 0.11% iBuOH, and 0.19%IBF.

As used herein, TBA is tertiary butyl alcohol, IPA is isopropanol, MEK is methyl ethyl ketone, SBA is secondary butyl alcohol, TBF is tertiary butyl formate, iBuOH is isobutanol and IBF is isobutyl formate.

Beds 1 and 2 are operated such that while one bed is being filled with liquid to be treated, the other bed is being drained of contained liquid and while one bed is contacting the liquid feed and removing impurities therefrom, the other bed is being regenerated by passage of heated gas there through.

FIG. 1 illustrates operation where the feed TBA stream passes via line 3 through open valve 4 into contact vessel 1 wherein impurities are removed by adsorption on the Zeolite 13X. The treated TBA stream reduced in impurities is removed via line 5 through open valve 6 to a product storage tank.

While the TBA stream is treated in vessel 1 as above indicated, the packed bed of Zeolite 13X in vessel 2 is being regenerated by passage there through of heated nitrogen. Nitrogen containing removed impurities is passed from vessel 2 through valve 10 and via line 11 to cooler 12 wherein the stream is cooled from about 300° C. to 40° C. The cooled stream passes via line 13 to vapor/liquid separator 14, and condensate comprising the removed impurities is removed via line 15.

The vapor stream mainly comprised of nitrogen passes from separator 14 via line 16 and blower 17 to heater 7 wherein the vapor is heated to 328° C. The heated vapor passes via line 8 and valve 9 to vessel 2 wherein it contacts the Zeolite 13X bed, removing adsorbed impurities from the Zeolite 13X. Make up nitrogen is provided as needed.

After a certain time on stream, the Zeolite 13X in vessel 1 falls to a predetermined level of impurities removal, indicating that the adsorbent should be regenerated. According to the present invention, liquid is drained from vessel 1 while at the same time liquid feed fills vessel 2 which contains the regenerated adsorbent.

Referring to FIG. 2, liquid feed TBA passes via line 21 through valve 20 to fill the adsorbent bed in vessel 2 while liquid TBA is drained from vessel 1 through valve 18 and line 26 to recycle. As a feature of the invention, as vessel 2 is filling, nitrogen is forced out of vessel 2 through valve 9 and passes via line 22 through valve 19 to vessel 1 wherein this introduced nitrogen aids in the process of draining liquid from vessel 1.

When the draining of vessel 1 and the filling of vessel 2 is complete, operation resumes as shown in FIG. 3 with the TBA feed stream passing via line 21 through valve 20 to vessel 2 wherein the TBA feed contacts the regenerated Zeolite 13X and impurities are removed. The treated TBA from which the impurities have been removed passes from vessel 2 via valve 23 and line 5 to the product tank.

At the same time Zeolite 13X in vessel 1 is being regenerated by passage there through of heated nitrogen in the same fashion previously described for vessel 2. Heated nitrogen passes via line 8 and valve 19 into vessel 1 wherein it removes impurities from the Zeolite 13X adsorbent. Nitrogen containing the impurities passes from vessel 1 via valve 24 and line 11 to the cooler 12, separator 14, blower 17 and heater 7 as previously described. Heated nitrogen circulates via line 8 and valve 19 back to vessel 1 for impurities removal.

When the adsorptive capacity of the Zeolite 13X in vessel 2 is sufficiently depleted, vessel 2 is drained and vessel 1 is filled in a fashion similar to that previously described. Referring to FIG. 4, liquid is drained from vessel 2 and recycled via valve 25 and line 26. At the same time, liquid feed is passed via line 3 and valve 4 to fill vessel 2. Nitrogen from vessel 1 passes via valve 19, line 22 and valve 9 to vessel 2 to assist in forcing the liquid from vessel 2.

When the draining and refilling is complete, operation resumes as described in FIG. 1.

As a result of practice of the invention, substantial economies are achieved. Productivity is maximized by operating the beds in parallel. Economy of nitrogen use is achieved since, if the beds were to be drained and filled independently, nitrogen would be needed to replace drained liquid and then vented placing a substantial burden on a plant disposal system and requiring nitrogen replenishment.

I claim:

1. In a process for removing impurities from a liquid by contact with a solid adsorbent using parallel contact adsorbent beds wherein when one bed is contacting the liquid the parallel bed is being regenerated by contact with heated inert gas, the improvement wherein during changeover inert gas is transferred from the regenerated bed to the spent bed during the period that liquid is being drained from the spent bed.

2. The process of claim 1 wherein the liquid from which impurities are removed is primarily tertiary butyl alcohol.

3. The process of claim 1 wherein the solid adsorbent is Zeolite 13X.

4. The process of claim 1 wherein the inert gas is nitrogen.

* * * * *